(12) United States Patent
Quintanilha

(10) Patent No.: US 9,904,181 B2
(45) Date of Patent: Feb. 27, 2018

(54) INSPECTION APPARATUS AND METHOD, LITHOGRAPHIC APPARATUS, LITHOGRAPHIC PROCESSING CELL AND DEVICE MANUFACTURING METHOD

(71) Applicant: ASML Netherlands B.V., Veldhoven (NL)

(72) Inventor: Richard Quintanilha, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 91 days.

(21) Appl. No.: 14/901,993

(22) PCT Filed: Jun. 13, 2014

(86) PCT No.: PCT/EP2014/062338
§ 371 (c)(1),
(2) Date: Dec. 29, 2015

(87) PCT Pub. No.: WO2015/000673
PCT Pub. Date: Jan. 8, 2015

(65) Prior Publication Data
US 2016/0377990 A1    Dec. 29, 2016

Related U.S. Application Data

(60) Provisional application No. 61/842,430, filed on Jul. 3, 2013.

(51) Int. Cl.
*G03B 27/54* (2006.01)
*G03F 7/20* (2006.01)
*G01N 21/956* (2006.01)

(52) U.S. Cl.
CPC ... *G03F 7/70625* (2013.01); *G01N 21/95623* (2013.01); *G03F 7/70633* (2013.01);
(Continued)

(58) Field of Classification Search
CPC ....... G01N 21/95623; G01N 2201/061; G01N 2201/08; G01N 2201/12; G03F 7/70625; G03F 7/70633
(Continued)

(56) References Cited

U.S. PATENT DOCUMENTS 6,772,084 B2    8/2004    Bischoff et al.
2006/0033921 A1    2/2006    Den Boef et al.
(Continued)

FOREIGN PATENT DOCUMENTS

| CN | 101165597 A | 4/2008 |
| CN | 101251718 A | 8/2008 |

(Continued)

OTHER PUBLICATIONS

English-language abstract for Chinese Patent Publication No. 101165597 A, published Apr. 23, 2008; 1 page.
(Continued)

*Primary Examiner* — Peter B Kim
(74) *Attorney, Agent, or Firm* — Sterne, Kessler, Goldstein & Fox P.L.L.C.

(57) ABSTRACT

The present invention determines property of a target (30) on a substrate (W), such as a grating on a wafer. An inspection apparatus has an illumination source (702, 710) with two or more illumination beams (716, 716', 716", 716''') in the pupil plane of a high numerical aperture objective lens (L3). The substrate and target are illuminated via the objective lens from different angles of incidence with respect to the plane of the substrate. In the case of four illumination beams, a quad wedge optical device (QW) is used to separately redirect diffraction orders of radiation scattered from the substrate and separates diffraction orders from the two or more illumination beams. For example four $0^{th}$ diffraction orders are separated for four incident directions. After cap-
(Continued)

ture in multimode fibers (MF), spectrometers (S1-S4) are used to measure the intensity of the separately redirected $0^{th}$ diffraction orders as a function of wavelength. This may then be used in determining a property of a target.

18 Claims, 7 Drawing Sheets

(52) U.S. Cl.
CPC ... *G01N 2201/061* (2013.01); *G01N 2201/08* (2013.01); *G01N 2201/12* (2013.01)

(58) Field of Classification Search
USPC .......................................................... 355/67
See application file for complete search history.

(56) References Cited

U.S. PATENT DOCUMENTS

| | | |
|---|---|---|
| 2006/0197951 A1 | 9/2006 | Frommer et al. |
| 2007/0091327 A1 | 4/2007 | Xu et al. |
| 2007/0114678 A1 | 5/2007 | Van Haren et al. |
| 2008/0198380 A1 | 8/2008 | Straaijer et al. |
| 2011/0125458 A1 | 5/2011 | Xu et al. |
| 2012/0206703 A1 | 8/2012 | Bhattacharyya et al. |
| 2014/0192338 A1 | 7/2014 | Den Boef |
| 2014/0233025 A1 | 8/2014 | Den Boef et al. |

FOREIGN PATENT DOCUMENTS

| | | |
|---|---|---|
| CN | 101903832 A | 12/2010 |
| JP | 2002-506198 A | 2/2002 |
| JP | 2006-060214 A | 3/2006 |
| TW | 200302538 | 8/2003 |
| TW | 200616133 | 6/2006 |
| TW | 200732866 | 9/2007 |
| WO | WO 03/089872 A2 | 10/2003 |

OTHER PUBLICATIONS

International Search Report directed to related International Patent Application No. PCT/EP2014/062338, dated Oct. 21, 2014; 5 pages.

International Preliminary Report on Patentability and Written Opinion of the International Searching Authority directed to related International Patent Application No. PCT/EP2014/062338, dated Jan. 5, 2016; 7 pages.

Yeung Joon Sohn et al. "193 nm Angle-Resolved Scatterfield Microscope for Semiconductor Metrology." Proc. SPIE 7405, Instrumentation, Metrology, and Standards for Nanomanufacturing III, 74050R (Aug. 24, 2009); 8 pages.

Deh-Ming Shyu et al. "Angle-Resolved Scatterfield Microscope for Linewidth Measurement." Proc. SPIE 7272, Metrology, Inspection, and Process Control for Microlithography XXIII, 72721L (Mar. 24, 2009); 10 pages.

English-language abstract for Taiwanese Pub. No. 200616133, published Jun. 16, 2006; 1 page.

INSPECTION APPARATUS AND METHOD, LITHOGRAPHIC APPARATUS, LITHOGRAPHIC PROCESSING CELL AND DEVICE MANUFACTURING METHOD

CROSS-REFERENCE TO RELATED APPLICATIONS

This application claims the benefit of U.S. provisional application 61/842,430, which was filed on Jul. 3, 2013 and which is incorporated herein in its entirety by reference.

FIELD

The present invention relates to apparatus and methods for determining properties in microstructures usable, for example, in the manufacture of devices by lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between successive layers formed in or on the patterned substrate and critical linewidth of developed photosensitive resist. This measurement may be performed on a product substrate and/or on a dedicated metrology target. There are various techniques for making measurements of the microscopic structures formed in lithographic processes, including the use of scanning electron microscopes and various specialized tools. A fast and non-invasive form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

In lithographic processes, it is necessary frequently to make measurements of the structures created, e.g., for process control and verification. Various tools for making such measurements are known, including scanning electron microscopes, which are often used to measure critical dimension (CD) Various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis. In this type of measurement devices measurements information is collected in the pupil plane of the measurement branch.

Properties of gratings, such as overlay or CD, can also be measured in an image plane of the measurement branch of a measurement device. This is the case for Angle Resolved Imaging Microscopy (ARIM). In the ARIM method light is directed to the target under a certain angle of incidence (AOI) resulting in a measured image. After this measurement the angle of incidence is modified and another measurement takes place using light that is incident on the target with the modified angle. The images that are captured in this way can be used for reconstruction of the measured target. The ARIM method enables to measure relatively small targets.

SUMMARY

According to an aspect of the present invention, there is provided an apparatus for determining a property of a target on a substrate, the apparatus comprising: an illumination system configured to provide radiation; an optical system comprising an objective, and configured to illuminate the target via the objective with two or more illumination beams; an optical device configured to separately redirect diffraction orders resulting from the illumination of the target with the two or more illumination beams; one or more detectors in an image plane, the one or more detectors configured to measure one or more properties of the separately redirected diffraction orders; a processor configured to determine the property of the target using the measured one or more properties of the separately redirected diffraction orders.

According to another aspect of the present invention, there is provided a method of determining a property of a target on a substrate, the method comprising illuminating the target via an objective with radiation of two or more illumination beams, separately redirecting zero diffraction orders of radiation scattered from said substrate; measuring one or more properties of the separately redirected zero diffraction orders using one or more detectors; and determining the property of the target using the measured one or more properties of the separately redirected zero diffraction orders.

According to another aspect of the present invention, there is provided a lithographic apparatus comprising: an illumination system arranged to illuminate a pattern; a projection system arranged to project an image of the pattern on to a substrate; and an inspection apparatus for determining a property of a target on a substrate. The inspection apparatus comprising: an illumination system configured to provide radiation; an optical system comprising an objective, and configured to illuminate the target via the objective with two or more illumination beams; an optical device configured to separately redirect diffraction orders resulting from the illumination of the target with the two or more illumination beams; one or more detectors in an image plane, the one or more detectors being configured to measure one or more properties of the separately redirected diffraction orders; a processor configured to determine the property of the target using the measured one or more properties of the separately redirected diffraction orders.

According to another aspect of the present invention, there is provided a lithographic cell comprising: a coater arranged to coat substrates with a radiation sensitive layer; a lithographic apparatus arranged to expose images onto the radiation sensitive layer of substrates coated by the coater; a developer arranged to develop images exposed by the lithographic apparatus; and an inspection apparatus for determining a property of a target on a substrate. The inspection apparatus comprising an illumination system configured to provide radiation; an optical system comprising an objective, and configured to illuminate the target via the objective with two or more illumination beams; an optical device configured to separately redirect diffraction orders resulting from the illumination of the target with the two or more illumination beams; one or more detectors in an image plane, the one or more detectors being configured to measure one or more properties of the separately redirected diffraction orders; a processor configured to determine the property of the target using the measured one or more properties of the separately redirected diffraction orders.

According to another aspect of the present invention, there is provided a device manufacturing method comprising: using a lithographic apparatus to form a pattern on a substrate; and determining a value related to a parameter of the pattern by: providing radiation; illuminating the target via an objective with the radiation of two or more illumination beams; separately redirecting zero diffraction orders of radiation scattered from said substrate; measuring one or more properties of the separately redirected zero diffraction orders using one or more detectors; and determining the value related to a parameter of the pattern using the measured one or more properties of the separately redirected zero diffraction orders.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying schematic drawings in which corresponding reference symbols indicate corresponding parts, and in which.

Figure 1:
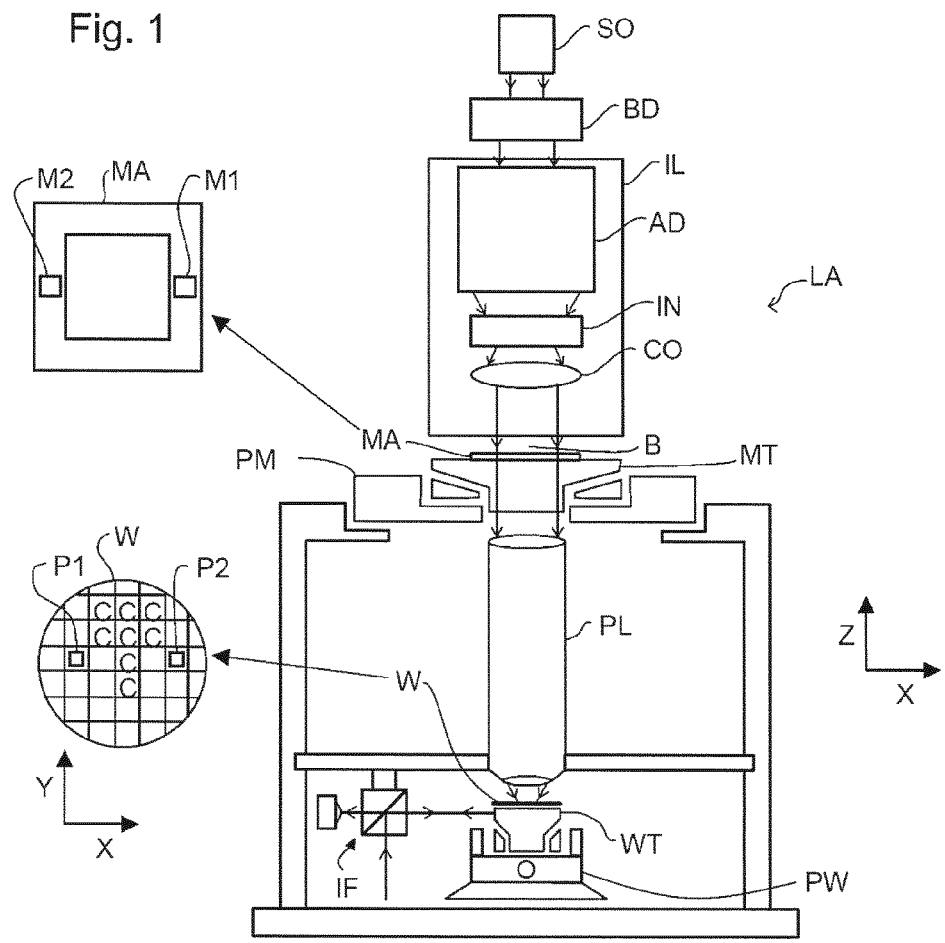
FIG. 1 depicts a lithographic apparatus.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals, and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

Embodiments of the present invention use a plurality of wavelengths (in parallel with a broadband light source or in series using a tunable monochromatic light source) and detecting intensity for different wavelengths for spatially separated diffraction orders.

FIG. 1 schematically shows a lithographic apparatus LAP including a source collector module SO according to an embodiment of the invention. The apparatus comprises: an illumination system (illuminator) IL configured to condition a radiation beam B (e.g., EUV radiation); a support structure (e.g., a mask table) MT constructed to support a patterning device (e.g., a mask or a reticle) MA and connected to a first positioner PM configured to accurately position the patterning device; a substrate table (e.g., a wafer table) WT constructed to hold a substrate (e.g., a resist-coated wafer) W and connected to a second positioner PW configured to accurately position the substrate; and a projection system (e.g., a reflective projection system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-) magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
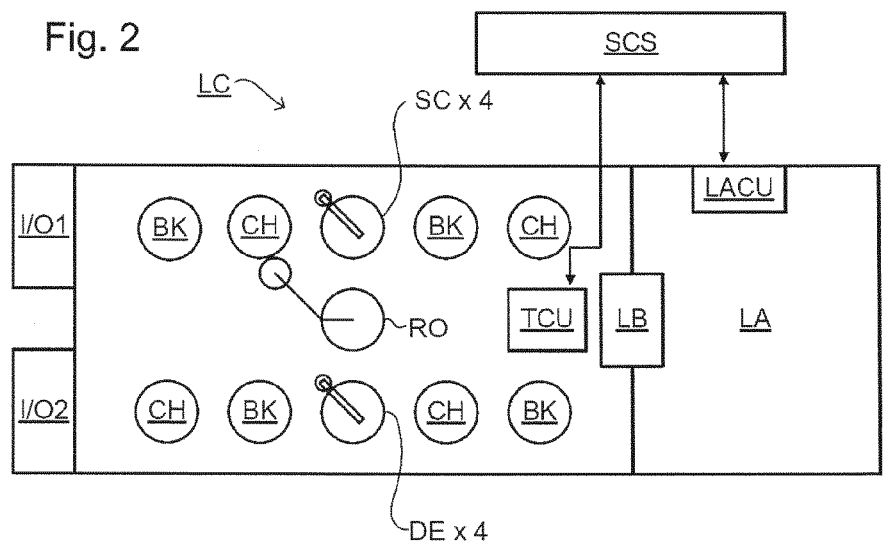
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
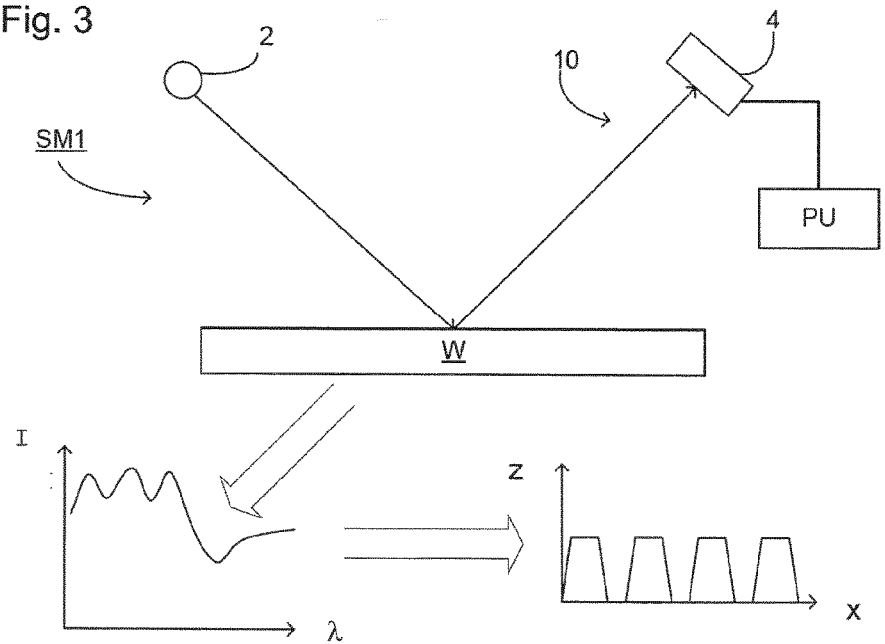
FIG. 3 depicts a first scatterometer.

FIG. 3 depicts a scatterometer which may be used in the present invention. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
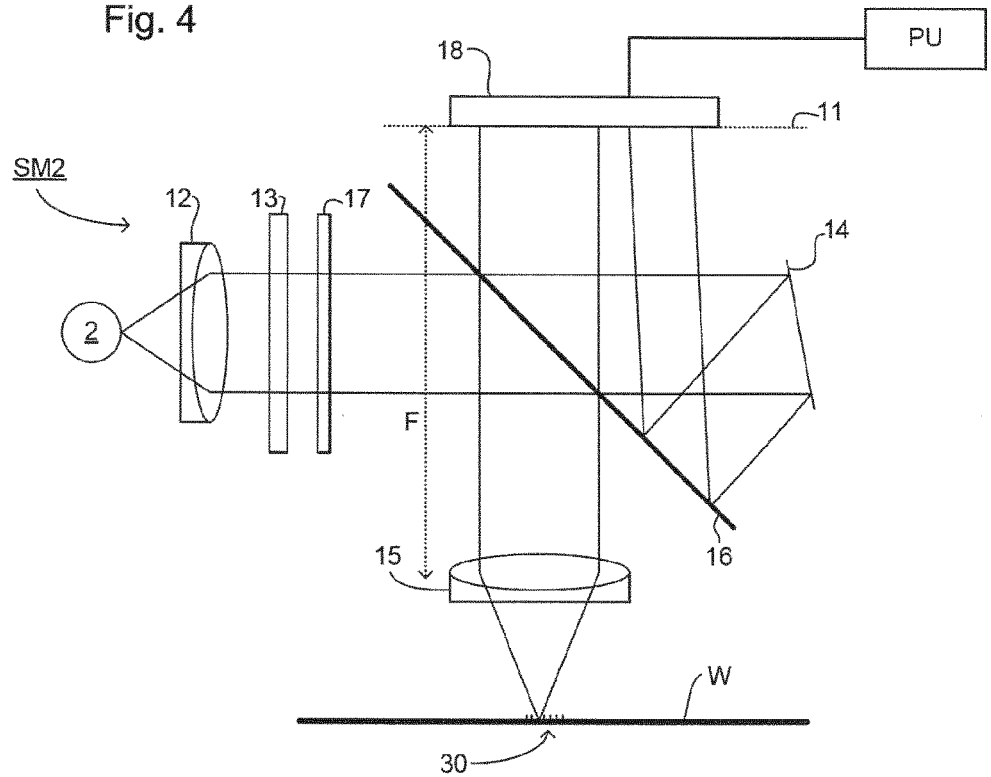
FIG. 4 depicts a second scatterometer.

Another scatterometer that may be used with the present invention is shown in FIG. 4. In this device, the radiation emitted by radiation source 2 is collimated using lens system 12 and transmitted through interference filter 13 and polarizer 17, reflected by partially reflected surface 16 and is focused onto substrate W via a microscope objective lens 15, which has a high numerical aperture (NA), e.g., at least 0.9 or at least 0.95 Immersion scatterometers may even have lenses with numerical apertures over 1. The reflected radiation then transmits through partially reflecting surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. Alternatively, the detector can be located at an image plane. In one example, the detector is a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18 or alternatively on to a different detector (not shown).

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e., one with a wide range of light frequencies or wavelengths—and therefore of colors) is possible, which gives a large etendue, allowing the mixing of multiple wavelengths. The plurality of wavelengths in the broadband each has a bandwidth of $\Delta\lambda$ and a spacing of at least 2 $\Delta\lambda$ (i.e., twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

As described above, the target is on the surface of the substrate. This target will often take the shape of a series of lines in a grating or substantially rectangular structures in a 2-D array. The purpose of rigorous optical diffraction theories in metrology is effectively the calculation of a diffraction spectrum that is reflected from the target. In other words, target shape information is obtained for CD (critical dimension) uniformity metrology. CD uniformity is a measurement of the uniformity of the grating on the spectrum to determine how the exposure system of the lithographic apparatus is functioning. Specifically, CD, or critical dimension, can be the width of the object that is "written" on the substrate and is the limit at which a lithographic apparatus is physically able to write on a substrate.

Figure 5:
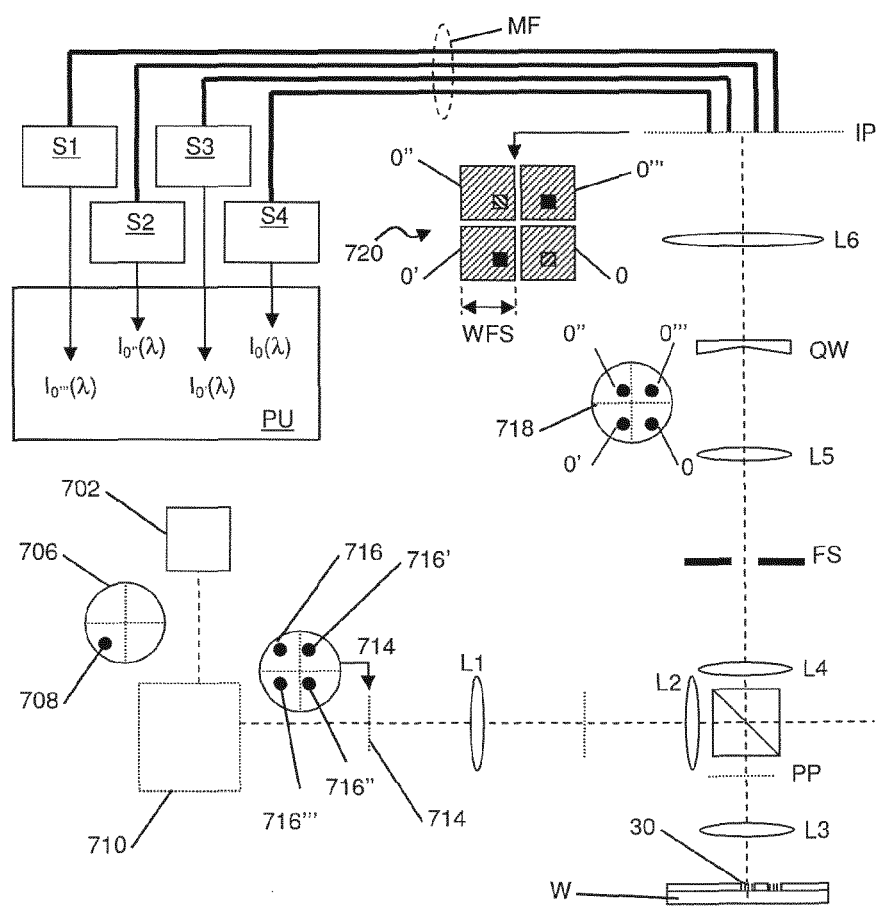
FIG. 5 depicts an embodiment of the invention.

The present invention relates to embodiments of apparatus for determining critical dimensions (CD) of periodic targets, such as gratings, FIG. 5 illustrates an inspection apparatus according to an embodiment of the present invention. With reference to FIG. 5, a broadband light source 702 provides a narrow pencil beam of white light, providing a plurality of wavelengths of radiation. The plurality of wavelengths are thus provided simultaneously, for fast measurement by the apparatus. In another embodiment, a tunable light source provides different wavelengths at different times. The light source 702 may, for example, be a white-light laser or a Xenon lamp. The illumination pupil 706 at the exit of the illuminator has one spot 708. The pencil beam is sent through a device 710. For example, the device 710 comprises number of (e.g., four) apertures. The illumination pupil plane 714 that exits the device 710 is illuminated with four identical white-light sources 716, 716', 716" and 716''' This provides a well-defined angle of incidence of illumination across the target that facilitates grating reconstruction. For this reason, the extent of the point sources is kept small. The position of the white-light sources 716, 716', 716" and 716''' can be chosen differently than in a square shape. For instance, any configuration wherein one white-light source is positioned in each pupil quadrant would be accurate. Also, the invention is not limited to the usage of four white-light sources. Also any other number (e.g., eight) of white-light sources would be accurate.

Lenses L1 and L2 form a double-telecentric system that image the illumination pupil into the pupil plane of the high-NA (numerical aperture) lens L3. This objective lens L3 illuminates the target 30 which may be a small grating that is surrounded by an unknown product pattern. Lenses L1, L2 and L3 thus form an optical system that illuminates the target via the objective. The illumination spot on the wafer is normally chosen much larger than the grating. Typical values are, for example, a spot diameter of 30 µm projected on the wafer and grating size of 10×10 µm². The embodiment will still work when the illumination spot is smaller than the grating, for example with a relatively large grating in a scribe lane.

Figure 6:
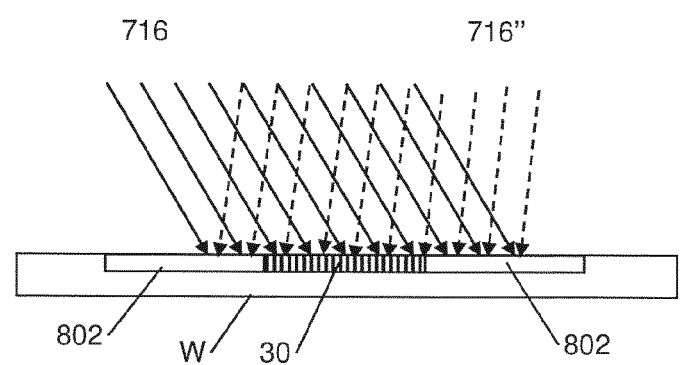
FIG. 6 illustrates light rays having different angles of incidence on the substrate.
Figure 7:
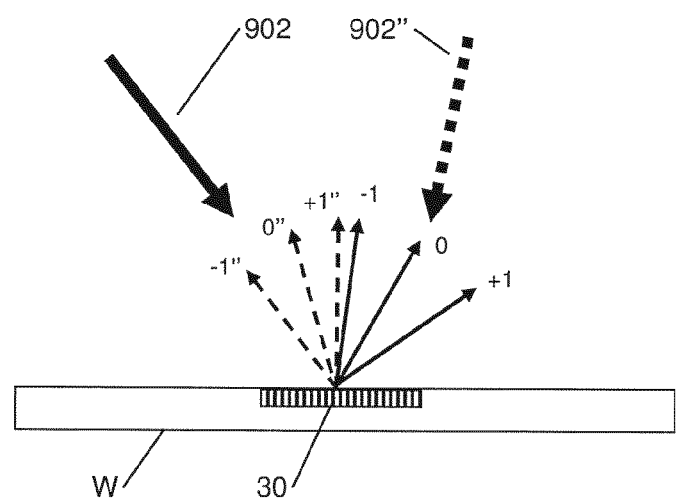
FIG. 7 illustrates two light beams incident on the target grating on the substrate and the resulting scattered diffraction orders.

FIG. 6 illustrates light rays incident on the substrate as a result from two of the four white-light sources (i.e., 716 and 716"). The solid arrows represent light rays coming from point 716 in the illumination plane 714. The dashed arrows represent light rays coming from point 716" in the illumination plane 714. As can be seen, the angle of incidence of the lights rays coming from point 716 is different than the angle of incidence of the light rays coming from 716". The substrate W has a target grating 30 surrounded by product areas 802. The illumination beam thus overfills the target grating 30. FIG. 7 illustrates two light beams incident on the target grating 30 on the substrate W and the resulting scattered diffraction orders. The solid arrow 902 represents a light ray coming from point 716 in the illumination plane 714. The solid arrows −1, 0 and +1 represent the scattered negative first order, zeroth order and positive first order diffracted beams respectively originating from the incident beam 902. The dashed arrow 902" represents a light ray coming from point 716" in the illumination plane 714. The dashed arrows −1', 0' and +1' represent the scattered negative first order, zeroth order and positive first order diffracted beams respectively originating from the incident beam 902'. Each of the scattered beams has a band of wavelengths of light because a white light source is used. For measuring properties, such as critical dimension, of target grating 30 in particular the zero order diffracted beams are of interest. It can be seen in FIG. 7 that the zero order beams 0 and 0" each reflect from the grating target 30 under a different angle. The same holds for the zero order beams as a result of lights rays coming from points 716' and 716'" (not depicted is FIGS. 6 and 7). The angle of reflection depends on the position of the corresponding white-light source in the respective quadrant of the illumination pupil. The shape of the grating will affect the zeroth orders as a result of which critical dimensions (CD) can be measured.

Because different positions in the illumination pupil of the white-light sources result in different angles of incidence, the angles of incidence can be chosen that are the most sensitive for the to be measured properties of the target grating 30. In other words, the zero order information that an increased sensibility for certain characteristics, such as CD, of the target grating 30 can be selected according to the present invention.

With reference again to FIG. 5, the light that is scattered by the target grating 30 and the surrounding product area is collimated by lens L3 and the double telecentric system L3 and L4 make a magnified image of the grating and product environment on the field stop FS. The field stop FS is placed at the image plane of the objective lens L3. The purpose of the field stop FS is to limit the spatial extent of the intermediate image and to suppress stray light in the detection optics. The spatial filter thus spatially filters radiation scattered from a surface of the substrate adjacent to the target to select radiation scattered by the target.

Lenses L4 and L5 re-image the pupil plane PP of the scattered light onto an achromatic quadrature wedge QW. This image 718 of the pupil plane has the zero diffraction orders resulting from the incident beams 716, 716', 716" and 716'". The quadrature wedge QW redirects the light in the four quadrants of the pupil plane 718 in four different directions. Thus the quadrature wedge QW is an optical device configured to separately redirect diffraction orders of radiation scattered from the substrate. The quadrature wedge QW may comprise four wedges. As a result of the quadrature wedge QW, lens L6 produces, in the image plane IP, four spatially separated sub images 720 of the light that is transmitted by the aperture stop FS. Each of the four sub images 720 are the width WFS of the field stop FS. The central square in each sub-image represents the target grating and is surrounded by the product circuitry. Although the target grating is shown as a square, it may have another shape, such as a rectangle. The images 720 comprise the zeroth order images 0, 0', 0" and 0'" resulting from respectively incident beams 716, 716', 716" and 716'". The skilled person will appreciate that the arrangement of each of the four sub images in the image plane will depend on the wedge arrangement. Other arrangement of the sub images can therefore be achieved using different relative orientation of the wedges and/or one or more lenses L6. Furthermore, the sub images need not be arranged on the same plane.

As white light is used, the quadrature wedge is achromatic otherwise the image shift would become color-dependent. Achromatic wedges can be made in transmission but reflective wedges are also suitable since they are intrinsically achromatic.

Four multimode detection fibers MF are now used to capture the zero order intensity components. Thus the fibers are a capturing device configured to capture one or more of the separately redirected zero diffraction orders. This is "selected area" detection that suppresses light from the product environment. The position of the fibers relative to the lenses is configured to capture the selected area of each sub image 720 corresponding to the target grating. Optionally, piezo micro manipulators may be used for a dynamic adjustment in the sensor.

Multimode fibers typically have core diameters of 200 µm and this diameter is smaller than the image of the grating in order to select light scattered by the grating in preference to that scattered by the surrounding product area. If the grating has a length of 10 µm then the magnification of the lens system L3, L4, L5 and L6 in this embodiment is at least 40.

The wedge angle is sufficiently large to allow a complete separation of the four sub images 720. If the separation is too small the images will overlap causing crosstalk from the product area into the grating area.

The broadband light that is captured by the detection fibers is sent to four spectrometers (S1-S4) that are nominally identical. These four spectrometers simultaneously and in parallel measure the intensities of the four zero diffraction orders as a function of the wavelength. For example, a typical wavelength range could be 400-800 nm with a spectral resolution of 5 nm. This yields 80 pixels per spectrum so a grand total of about 320 samples. This measurement at the plurality of the wavelengths λ in the broadband light source can be acquired with very short acquisition times which enables high throughput. Because several (in this embodiment four) zero diffraction orders can be measured simultaneously and the zero diffraction orders result from incident beams with different angles of incidence (AOI), the throughput of the measurement is improved.

The set of measured spectra can now be used in processor PU to calculate a property, such as CD, of the target grating. Instead of using a white-light source, a single wavelength source can be used. The single wavelength source may be tunable or switchable to provide a plurality of wavelengths. For each single wavelength an image is projected on a detector such as a CCD camera which measures the intensities of the images formed by the four zero orders. In such an embodiment a pattern recognition software module executing on the processing unit PU is used to identify the area where the grating images are located and to extract the intensities zero orders at a particular wavelength. The wavelength is thus adjusted and the measurements are repeated in series to determine the intensities of the four zero orders a plurality of the single wavelengths.

It is also possible to make a more complex illumination associated with a multi-wedges prism. For instance, this method can be easily extended to 8 wedges prism associated with an octupole illumination. This will enable an improvement of the throughput by a factor of 8 (and will limit the number of scans). It is in principle feasible to develop special multi-wedges and multi-poles illumination to avoid any scanning and perform the acquisition of all required data in one single measurement. A priori this will require a large CCD array to fit all images.

Figure 8:
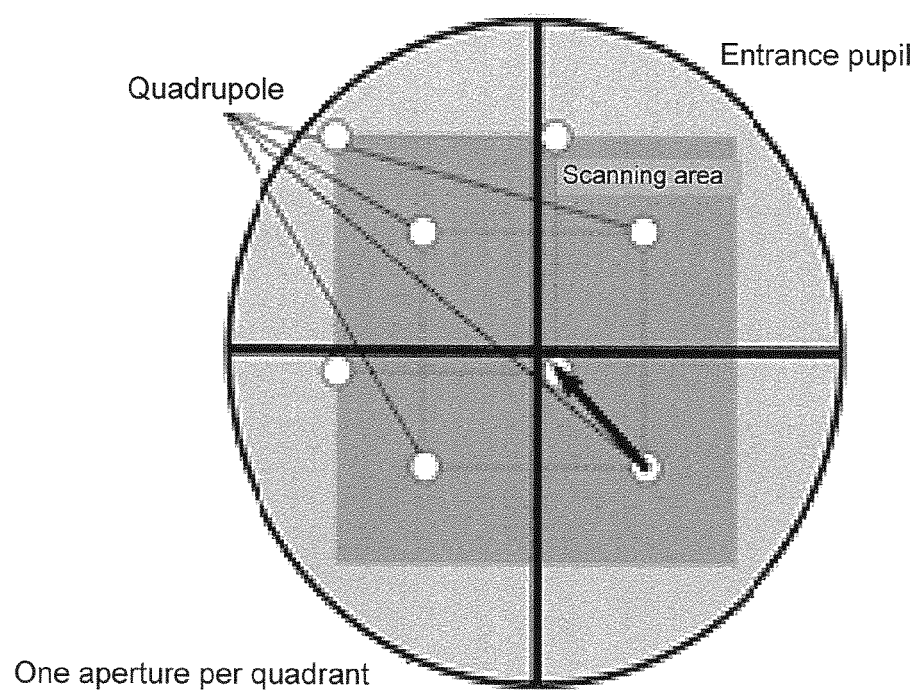
FIG. 8 illustrates the scanning of a quadruple across the illumination pupil.

More measurement information can be obtained if the illumination is scanned in the illumination pupil plane. FIG. 8 shows an example in case of quadruple illumination. Four illumination beams can be created by a single aperture in each pupil quadrant. The position of the four apertures can be of course chosen differently than in a square shape. The scanning of the quadruple can be done by a tilting mirror placed in the illumination field stop of the tool which will enable to scan the pupil with the quadruple. Another option is having a set of different quadruple in the wheel placed in the entrance pupil of the tool, or scanning the entrance pupil with the quadruple using the apertures holder wheel place in the entrance pupil of the tool.

Although the measurement and modeling of intensity of diffracted light as a function of frequency is described with reference to FIG. 5, embodiments of the present invention also include the measurement and modeling of the polarization state as a function of frequency using suitable ellipsometric or polarimetric techniques.

In an alternative embodiment, instead of using a white-light source a single wavelength source is used. The single wavelength source may be tunable or switchable to provide a plurality of wavelengths, and the sub images 720 are projected on a detector such as a CCD camera which measured the intensities of the images formed be the several $0^{th}$ diffraction orders. In such an embodiment a pattern recognition software module can be used to identify the area where the sub images 720 are located and to extract the intensities of the several $0^{th}$ diffraction orders.

Figure 9:
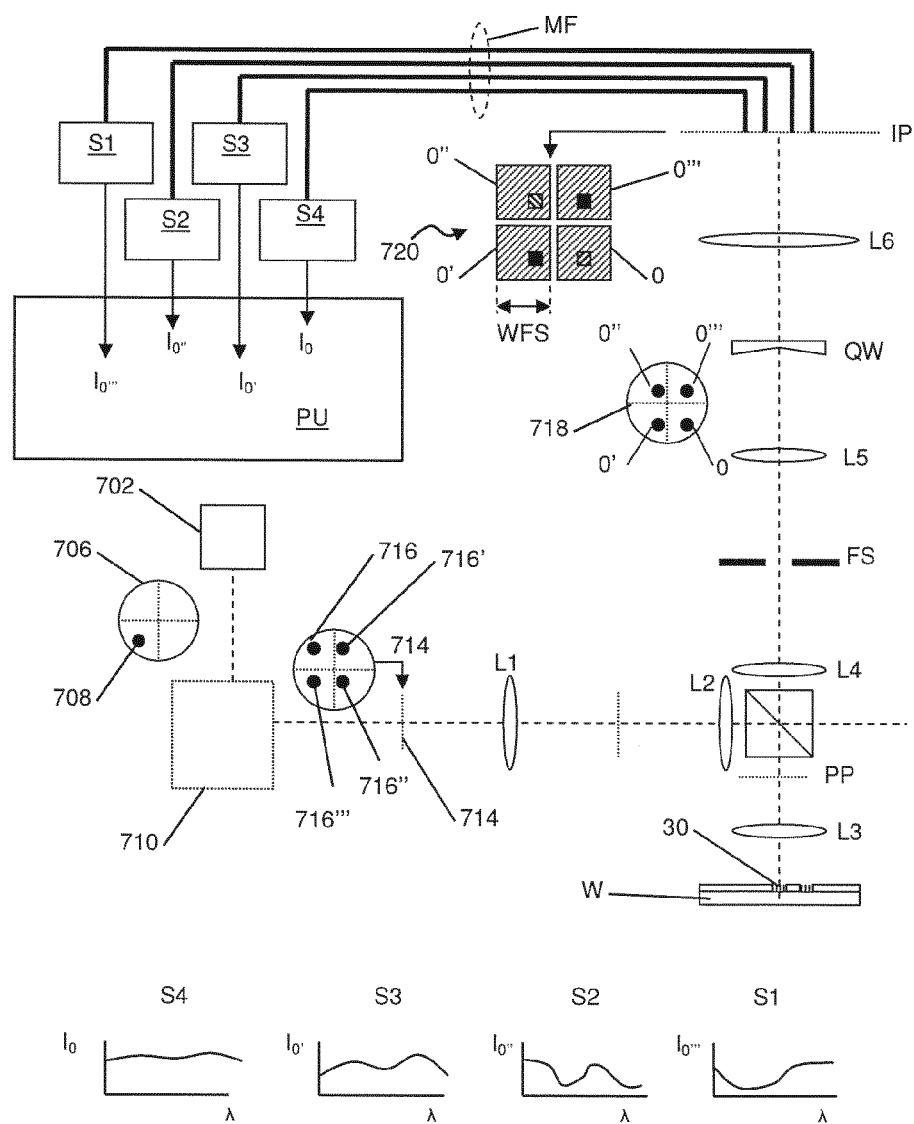
FIG. 9 illustrates another embodiment of the present invention.

A further improvement of the throughput can be achieved when a broadband source 702 is used and spectrometers S1-S4 are used that measure information at a plurality of wavelengths λ simultaneously (see FIG. 9). In FIG. 9 the same references are used as in FIG. 5. In such a configuration it will not be required to acquire many images as function of the AOI. For instance, if a spectrometer S has a spectral resolution of 5 nm and a broadband source 702 is used with a range of 400 nm to 750 nm that will result for each AOI to 70 measurement points. The wavelength dependent zero order intensities measured by the respective spectrometers S1-S4 are depicted at the lower part of FIG. 9.

A multimode detection fiber MF is used to capture the several (in this case four) $0^{th}$ order intensities. The multimode detection fiber MF may also function as a "selective area" detector. This ensures partially that light from the targets environment is suppressed. The fibers in the multimode fiber MF may for instance have a core from 200 μm to 2 mm although also other measures are possible. In general, depending of the tool magnification and the target size in the image the proper diameter core will be chosen. Different type of Fourier filtering can be used. The throughput can be increased by the use of achromatic wedge associated 4 optical fibers as detector and a quadruple in the illumination entrance pupil of the tool. That will enable to measure simultaneously 4 different angles of incidence.

The inspection apparatus and method of inspection embodiments described herein may be used in methods of device manufacturing and may be incorporated into lithographic apparatuses and lithographic processing cells.

Although specific reference may be made in this text to the use of inspection apparatus in the manufacture of ICs, it should be understood that the inspection apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. An apparatus for determining a property of a target on a substrate, the apparatus comprising:
   an optical system comprising an objective lens, and configured to illuminate the target via the objective lens with two or more illumination beams with different angles of incidence;
   an optical device configured to separately redirect diffraction orders resulting from the illumination of the target with the two or more illumination beams;
   one or more detectors in an image plane, the one or more detectors being configured to measure one or more properties of the separately redirected diffraction orders; and
   a processor configured to determine the property of the target using the measured one or more properties of the separately redirected diffraction orders.

2. The apparatus of claim 1, wherein the two or more illumination beams are generated by two or more illumination sources, a position of a first one of the two or more illumination sources is not symmetric to a position of a second one of the two or more illumination sources with respect to an origin of a plane of the two or more illumination sources.

3. The apparatus of claim 1, wherein the optical device is configured to separate diffraction orders of radiation scattered from said substrate resulting from each of the two or more illumination beams.

4. The apparatus of claim 1, wherein the diffraction orders comprise four zero diffraction orders.

5. The apparatus of claim 4, wherein the optical device is configured to project the separated diffraction orders onto the one or more detectors to form spatially separated images of the target arising from different separated diffraction orders.

6. The apparatus of claim 1, wherein the illumination system comprises a broadband light source.

7. The apparatus of claim 1, wherein the illumination system comprises a tunable single-wavelength light source.

8. The apparatus of claim 1, wherein the optical system is configured to illuminate the target with four illumination beams and the optical device comprises four wedges configured to separately redirect radiation from each of four quadrants.

9. The apparatus of claim 1, wherein the optical device is achromatic.

10. The apparatus of claim 1, further comprising a capturing device configured to capture one or more of the separately redirected diffraction orders.

11. The apparatus of claim 10, wherein the capturing device comprises one or more optical fibers.

12. The apparatus of claim 1, wherein the measured properties comprise an intensity.

13. The apparatus of claim 1, wherein the one or more detectors comprises a spectrometer.

14. The apparatus of claim 13, wherein the spectrometer is configured to measure the one or more properties of the separately redirected diffraction orders at a plurality of wavelengths simultaneously.

15. A method of determining a property of a target on a substrate, the method comprising:
   illuminating the target via an objective lens with radiation of two or more illumination beams with different angles of incidence;
   separately redirecting zero diffraction orders of radiation scattered from said substrate;
   measuring one or more properties of the separately redirected zero diffraction orders using one or more detectors; and
   determining the property of the target using the measured one or more properties of the separately redirected zero diffraction orders.

16. A lithographic apparatus comprising:
   an illumination system configured to illuminate a pattern;
   a projection system configured to project an image of the pattern on to a substrate; and
   an inspection apparatus configured to determine a property of a target on the substrate, the inspection apparatus comprising:
      an optical system comprising an objective lens, and configured to illuminate the target via the objective lens with two or more illumination beams with different angles of incidence;
      an optical device configured to separately redirect diffraction orders resulting from the illumination of the target with the two or more illumination beams;
      one or more detectors in an image plane, the one or more detectors being configured to measure one or more properties of the separately redirected diffraction orders; and
      a processor configured to determine the property of the target using the measured one or more properties of the separately redirected diffraction orders.

17. A lithographic cell comprising:
   a coater arranged to coat substrates with a radiation sensitive layer;
   a lithographic apparatus arranged to expose images onto the radiation sensitive layer of substrates coated by the coater;
   a developer arranged to develop images exposed by the lithographic apparatus; and
   an inspection apparatus for determining a property of a target on a substrate, the inspection apparatus comprising:
      an optical system comprising an objective lens, and configured to illuminate the target via the objective lens with two or more illumination beams with different angles of incidence;
      an optical device configured to separately redirect diffraction orders resulting from the illumination of the target with the two or more illumination beams;

one or more detectors in an image plane, the one or more detectors being configured to measure one or more properties of the separately redirected diffraction orders; and a processor configured to determine the property of the target using the measured one or more properties of the separately redirected diffraction orders.

18. A device manufacturing method comprising:

using a lithographic apparatus to form a pattern on a substrate; and determining a value related to a parameter of the pattern by:

illuminating the target via an objective lens with the radiation of two or more illumination beams with different angles of incidence;

separately redirecting four zero diffraction orders of radiation scattered from the substrate;

measuring one or more properties of the separately redirected four zero diffraction orders using one or more detectors; and determining the value related to a parameter of the pattern using the measured one or more properties of the separately redirected four zero diffraction orders.

* * * * *